US006679848B2

(12) United States Patent
Arling et al.

(10) Patent No.: US 6,679,848 B2
(45) Date of Patent: Jan. 20, 2004

(54) METHOD FOR ALLOWING PLUG-IN ARCHITECTURE FOR DIGITAL ECHOCARDIOGRAPHY LAB IMAGE PROCESSING APPLICATIONS

(75) Inventors: Robert S. Arling, North Andover, MA (US); Brian Collamore, Rutland, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/093,328

(22) Filed: Mar. 7, 2002

(65) Prior Publication Data

US 2003/0171679 A1 Sep. 11, 2003

(51) Int. Cl.$^7$ ................................................. A61B 8/06
(52) U.S. Cl. ...................................................... 600/450
(58) Field of Search ................................ 600/407–471; 382/128, 130, 131, 132, 133, 240, 248, 276; 707/1, 10; 714/37, 48

(56) References Cited

U.S. PATENT DOCUMENTS

| 5,671,353 A | * | 9/1997 | Tian et al. ..................... 714/48 |
| 5,910,111 A | * | 6/1999 | Hunziker .................... 600/407 |
| 6,415,046 B1 | * | 7/2002 | Kerut, Sr. .................... 382/128 |
| 6,574,629 B1 | * | 6/2003 | Cooke et al. ................. 707/10 |

OTHER PUBLICATIONS

Educational Media Services, http://222.echoincntext.com/learn_anat_pisa.asp.

Michael A. Schmidt, et al., "Anatomic Validation of a Novel Method fro Left Ventricular Volume and Mass Measurements with Use of Real–Time 3–Dimensional Echocardiography", Journal of American Society of Echocardiography, vol. 14, No. 1, Jan. 2001.

"Agilent Technologies Announces Quantitative Echocardiography on SONOS 5500 Ultrasound System", http://www.agilent.com/about/newsroom/presrel/2001/28jun2001a.html American Society of Echocardiography, Jun. 28, 2001.

Quan Liang, "Boundary Detection in Cardiovascular Ultrasonic Images Based on Multiscale Dynamic Programming", http://www2.lib.chalmers.se/cth/diss/doc/9899/LiangQuan.html.

Acuson Corporation Introduces a New Enhanced Imaging Option for its Aspen Echocardiography System at ACC:, http://222.echo–web.com/html/technews–acusin.html.

Robert M. Iwanochko MD, et al., "In Vitro Analysis of Color Doppler Flow Using Proximal Isovelocity Surface Area Improved Flow Estimates Using a Non Hemispherical Model", http://sellensr.me.queensu.ca/McLeodpapers/iwanochko/index.htm.

Renata Smokiova et al., "Neural Network Modeling of Ultrasound Speckle", LSE Program, University of Louisville, KY 40247.

Brian Coley, "Native ™ Tissue Harmonic Imaging in Pediatric Sonography" http://www.ultrasound.com/literature/whitepapers/coleyl/coley.html.

* cited by examiner

Primary Examiner—Ali M. Imam
(74) Attorney, Agent, or Firm—John Vodopia

(57) ABSTRACT

A method of adding a new operation stored in a new operation module to software driving an echocardiographic review station, which performs (a) detecting, by the software driving the echocardiographic review station, a presence of a new operation module not previously present in the software; and (b) executing the new operation module from the software driving the echocardiographic review station.

42 Claims, 4 Drawing Sheets

METHOD FOR ALLOWING PLUG-IN ARCHITECTURE FOR DIGITAL ECHOCARDIOGRAPHY LAB IMAGE PROCESSING APPLICATIONS

BACKGROUND OF THE INVENTION

A hospital's echocardiography lab performs analysis on a patent's heart data. For example, a viewing station in the lab allows doctors and technicians to view medical images on computer terminals for purposes of medical diagnosis. Measurements and various functions can be made on the displayed images. For example, a heart image can be displayed from previously acquired image data, and a technician can automatically perform functions on the data. For example, a technician can automatically use a software package to compute and display a heart's density.

Heart images can be acquired by an ultrasound system, and the images can then be digitally transferred to an echocardiographic review station. The echocardiographic review station can receive the digital image, display it, and perform a number of operations on it.

New features and operations are commonly made available periodically. For example, a new feature may comprise an improved way to view a heart image, or new calculations on heart images.

In the past, when new features were desired to be added to a particular echocardiographic review station, the new features would have to be added directly into the source code. The end user of the software would then have to acquire the new source code and replace the previous version. This method is burdensome, as it typically requires substantial computing and/or operator time to install the new source code. A further problem with this method is that a developer is required to be familiar with the internal workings of the review station in order for him to develop software code to implement a new feature.

Therefore, what is needed is an easy way to add functionality to an echocardiographic review station.

SUMMARY OF THE INVENTION

In one embodiment, the present invention provides for allowing an echocardiographic review station to incorporate different modules without having to recompile or modify the software driving the echocardiographic review station itself. Additional modules are added by use of a plug-in architecture. Modules can be added as separate files which can be executed from software driving the echocardiographic review station itself. Thus, additional functionality can be provided to an echocardiographic review station with minimal effort on the part of the user or the system operator.

BRIEF DESCRIPTION OF THE DRAWINGS

The various objects and advantages of the invention will become apparent and more readily appreciated from the following description of the preferred embodiments, taken in conjunction with the accompanying drawings of which.

DESCRIPTION OF THE PREFERRED EMBODIMENTS

Figure 1:
FIG. 1 is one example of a screen shot illustrating one example of a menu screen of an echocardiographic review station.

Reference will now be made in detail to the present preferred embodiments of the present invention, examples of which are illustrated in the accompanying drawings, wherein like reference numerals refer to the like elements throughout.

The present invention allows a digital echocardiographic review station to easily added new functionality and operations. New functionality and operations can be added to the echocardiography system by using "plug ins."

EnConcert, by Philips Medical Systems, is one example of a software application used in echocardiography labs to drive an echocardiographic review station, allowing users to view and analyze cardiac ultrasound images acquired by ultrasound imaging devices. The images can typically be transmitted over a network to an echocardiographic review station (for example, an EnConcert server) in the course of a patient exam, but can also be transferred to the server via a computer readable storage medium, such as a magneto-optical disk. Once on the server, the images may be called up by echocardiographic review stations (for example EnConcert clients) which also reside on the network (or perhaps on the server itself). Once the images are on the server, they are then reviewed by the reading cardiologist and a diagnosis is made of the patient's condition. The server can typically display moving images, which the cardiologist can use to make his diagnosis. The result of this procedure is typically a report containing various diagnostic findings, comments, etc. An echocardiographic review station can typically perform such operations as measuring operations that measure physical characteristics based on the images and displaying ultrasound images including moving images. The viewing system performs any operation needed by a cardiologist and any other medical professionals to make diagnosis and medical conclusions.

FIG. 1 is one example of a screen shot illustrating one example of a menu screen of an echocardiographic review station. This screen shot provides an overview of all of the images stored for a patient study. One or more of the images my be selected by clicking on them, which results in that image being "played," or in other words starts a digital animation of that particular image which was acquired in digital form by ultrasound technology.

The thumbnail page of FIG. 1 is shown as an example of operations performed by an echocardiographic review station. Of course, many other operations not described herein are typically performed by such stations.

Figure 2:
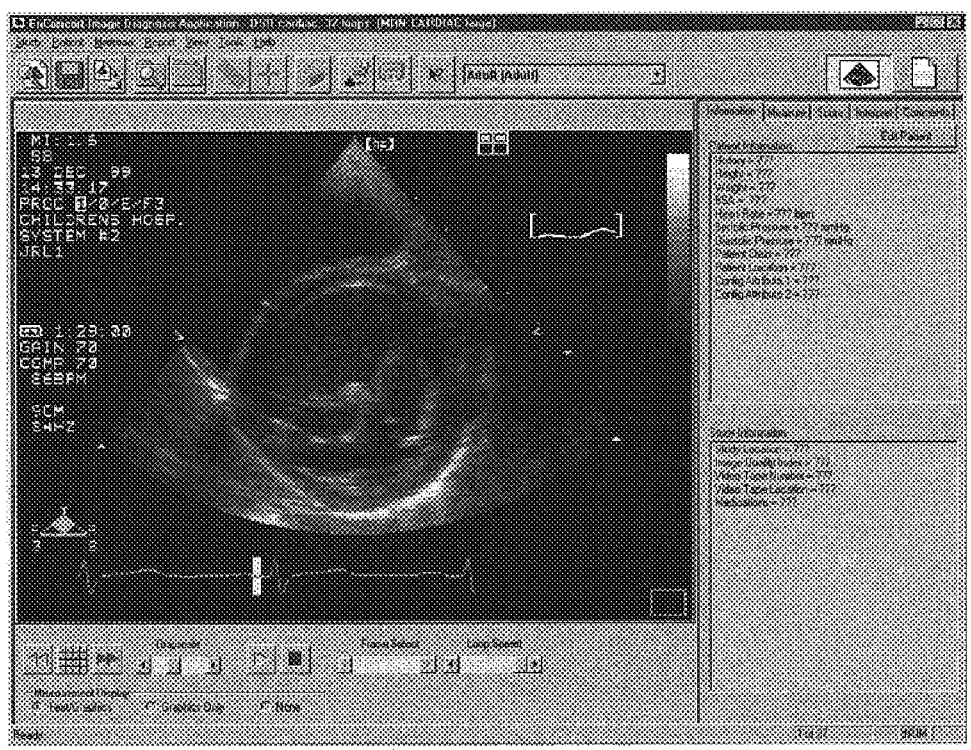
FIG. 2 is one example of a screen shot illustrating one example of an output of an echocardiographic review station.

FIG. 2 is one example of a screen shot illustrating one example of an output of an echocardiographic review station. A heart image 200 is displayed in the center, and might be displayed using moving images. A patient information window 202 contains patient information. A study information window 204 contains study information. Control buttons 204 on the bottom of the display allow an operator to control aspects of the display, such as forwarding, rewinding, adjusting image characteristics such as gray scale, etc.

Figure 3:
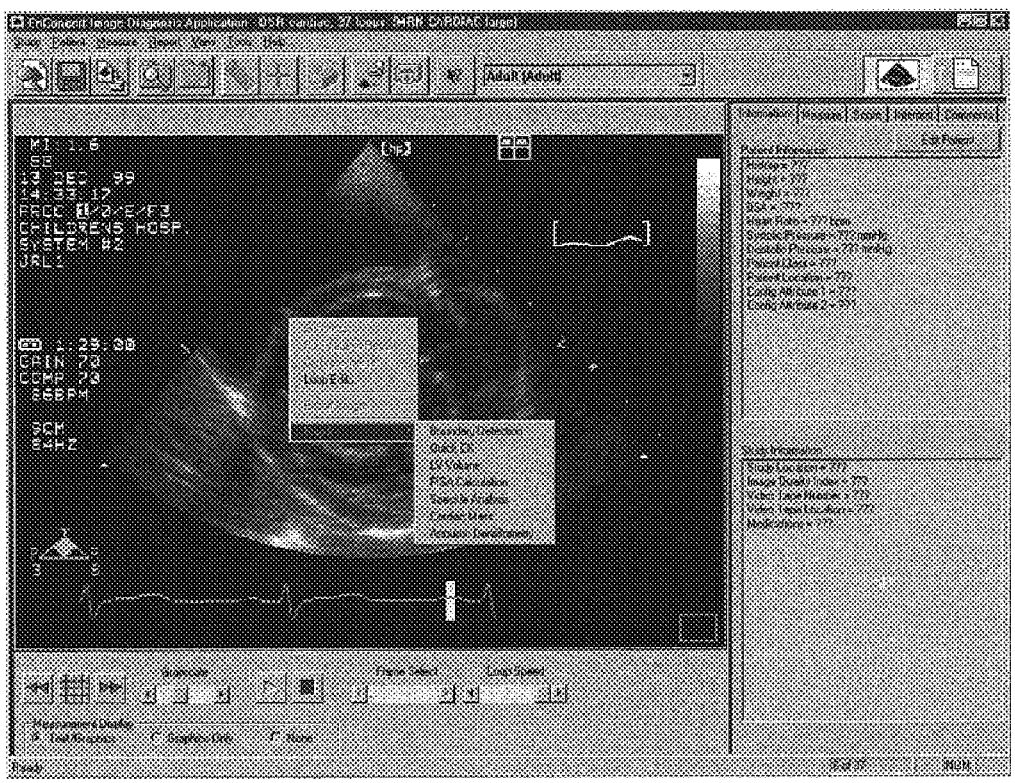
FIG. 3 is one example of a screen shot illustrating one example of how a particular plug in can be selected from the echocardiographic review station.

FIG. 3 is one example of a screen shot illustrating one example of how a particular plug in (or operation module)

can be selected from the echocardiographic review station. A function menu 302 can be displayed by using any one of a number of input methods. For example, a right click of a mouse can bring up the function menu 302, or else the function menu can be selected from the tool bar 304. On the function menu 302, a plug-in selection 304 is displayed. Upon selecting the plug-in selection 304, a plug in window 306 is displayed. The plug in window 306 displays all of the available plug-ins. Any of the plug ins displayed in the plug in window 306 can be executed by clicking the desired name for the plug in.

A new operation can be added to the echocardiographic review station in a number of different ways. A first way is to copy a program comprising an executable plug-in into a particular directory identified by the viewing software as containing plug-ins. The plug-ins can then be executed from this directory.

Figure 4:
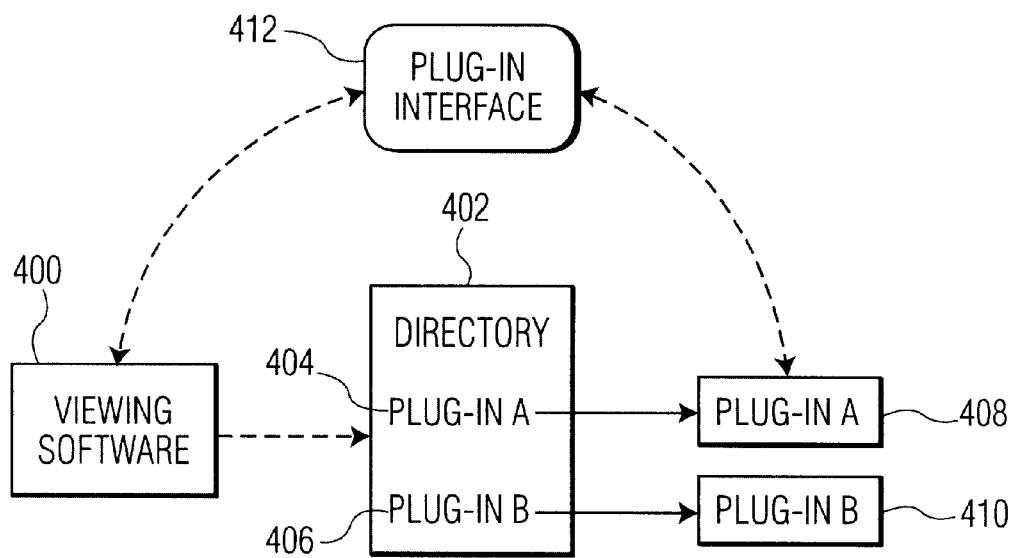
FIG. 4 is a block diagram illustrating one embodiment of how plug-ins can be executed according to the present invention.

FIG. 4 is a block diagram illustrating one embodiment of how plug-ins can be executed according to the present invention.

Viewing software 400, which is the software executing to receive, edit, and display the echocardiographic images (as discussed above), resides and executes on a computer system (not shown). A particular directory 402 (or directories) stores all of the plug ins loaded onto the system. For example, the directory 402 lists an entry for plug in A 404 and an entry for plug in B 406, the entries pointing to the actual locations of the files themselves. The files themselves, plug in A 408 and plug in B 410 are stored on the computer system.

When a user of the echocardiographic review station desires to execute a plug in and identifies the plug in, the software driving the echocardiographic review station will execute the actual plug in file. The plug in can either run simultaneously with the software (i.e. using a different process), or the processor can be temporarily dedicated to executing the plug in while the plug in executes.

In addition, the plug in may require resources or variables from the software itself. Therefore, a plug in interface 412 can assist the plug in with these matters. For example, the interface 412 can interactively transfer values such as variables and image data from the software as requested by the plug in while the plug in executes. The protocol for the interface 412 can be made publicly available, so that third parties can develop plug ins for the echocardiographic review station with ease.

Another way the plug in interface 412 can operate is a file can be specified by the plug in to the interface, which comprises a list of information necessary to interface with the viewing software. For example, the list can comprise image file names, calibration data for the image files, demographic data, etc. The plug in would then operate on the input data and produce results which may comprise modified image files or text pages. The results can then be displayed by the echocardiographic review station, or outputted to a separate file.

Figure 5:
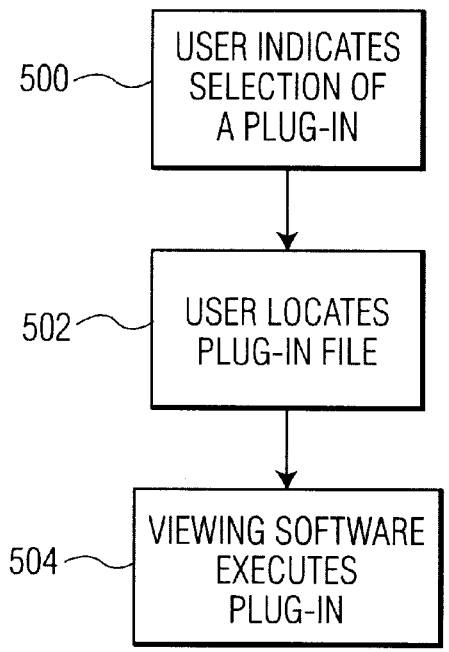
FIG. 5 is a flowchart illustrating another embodiment of how plug-ins can be executed according to the present invention.

FIG. 5 is a flowchart illustrating another embodiment of how plus-ins can be executed according to the present invention.

In operation 500, a user indicates a selection of a plug-in. This can be done, for example, by selecting a menu selection dedicated for execution of a plug in. As another example, a pointing device can be used to directly indicate that the user desires to execute a plug in. For example, a mouse can be right or left clicked.

From operation 500, once the user indicates that it is his desire to run a plug in, the process then proceeds to operation 502, wherein the user locates the plug in file. This can be done by identifying a particular directory on the system where a plug-in is located, or even by identifying a storage device (i.e. a floppy drive) that stores the desired plug in.

From operation 502, once the desired plug in is located, then the viewing software executes the plug in. The plug in can be executed simultaneously with the viewing software, or sequentially.

Further, note that a plug in may have a separate extension, identifying it as a plug in for a particular software package driving an echocardiographic review station (i.e. EnConcert).

Thus, there are many benefits of the above-described architecture. For example, the self encapsulated nature of plug ins allow for quick development and testing. When a plug in is added, only the plug in itself would need to be tested, not the entire viewing software.

In addition, the details of the plug in interface can be published so that third parties can develop and market plug ins, and users can mix and match plug in depending on their individual needs. Plus, unlike the current system in which the entire viewing software has to be recompiled or rebuilt before an addition can be made, using a plug in for this type of application means the developers of the plug in do not require internal knowledge of the software driving the echocardiographic review station.

Particular applications that plug ins can be used are, for example, computing a boundary detection which automatically detects a heart wall and other boundaries in an ultrasound image; an image analyzer which analyzes images produced by a color kinesis feature; a left ventricular volume calculation which analyzes a loop of images and calculates a volume of a left ventricle; a pisa calculation which calculates a surface area of a regurgitant jet; a speckle analysis which analyzes speck in an image; a cardiac mass calculation which calculates a cardiac mass from an image; and an acoustic densitometry calculation which calculates an acoustic densitometry of an image.

Any of the above calculations can be computed by conventional methods already publicly available in the prior art.

For examples of articles describing these calculations, see: Anatomic Validation of a Novel Method for Left Ventricular Volume and Mass Measurements with Use of Real-Time 3-Dimnesional Echocardiography, Michael A. Schmidt et al., J Am Soc Echocardiogr 2001;14:1–10; Neural Network Modeling of Ultrasound Speckle, Renata Smolikova, CSE Program, University of Louisville; In vitro Analysis of Color Doppler Flow Using Proximal Isovelocity Surface Area Improved Flow Estimates Using A Non Hemispherical Model, Robert M. Iwanochko, Division of Cardiology, Queens University, Kingston Ontario, Canada; Boundary Detection in Cardiovascular Ultrasonic Images Based on Multiscale Dynamic Programming, Quan Liang, School of Electrical and Computer Engineering, Chalmers University of Technology; Also see the web site for Philips Technologies at the time this Application is filed contains information on these calculations as well.

Although a few preferred embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A method of adding a new operation stored in a new operation module to software driving an echocardiographic review station, comprising:

detecting, by the software driving the echocardiographic review station, a presence of a new operation module not previously present in the software; and executing the new operation module from the software driving the echocardiographic review station.

2. A method as recited in claim 1, wherein the executing occurs without reloading the software.

3. A method as recited in claim 1, wherein the detecting checks a predetermined directory for presence of the new operation module.

4. A method as recited in claim 1, wherein the detecting is achieved by the presence of data produced by a preregistering of the new operation module with the software.

5. A method as recited in claim 1, wherein the detecting is achieved by manually calling the new operation module from within the software.

6. A method as recited in claim 1, wherein the echocardiographic review station displays moving cardiac images stored in digital form.

7. A method as recited in claim 1, wherein the new operation module comprises a module to execute along with the software driving the echocardiographic review station, the module manipulating or performing calculations relating to digital images acquired by an ultrasound imaging device.

8. A method as recited in claim 1, wherein the new operation module comprises a boundary detection operation which automatically detects a heart wall and other boundaries in an ultrasound image.

9. A method as recited in claim 1, wherein the new operation module comprises an image analyzer which analyzes images produced by a color kinesis feature.

10. A method as recited in claim 1, wherein the new operation module comprises a left ventricular volume calculation which analyzes a loop of images and calculates a volume of a left ventricle.

11. A method as recited in claim 1, wherein the new operation module comprises a pisa calculation which calculates a surface area of a regurgitant jet.

12. A method as recited in claim 1, wherein the new operation module comprises a speckle analysis which analyzes speckle in an image.

13. A method as recited in claim 1, wherein the new operation module comprises a cardiac mass calculation which calculates a cardiac mass from an image.

14. A method as recited in claim 1, wherein the new operation module comprises an acoustic densitometry calculation which calculates parameters related to the acoustic densitometry of an image.

15. An apparatus for adding a new operation stored in a new operation module to an echocardiographic review station, the apparatus comprising:

a detector detecting, by the echocardiographic review station, a presence of a new operation module not previously present on the echocardiographic review station; and an execution unit executing the new operation module from software driving the echocardiographic review station.

16. An apparatus as recited in claim 15, wherein the executing occurs without reloading the software.

17. An apparatus as recited in claim 15, wherein the detecting checks a predetermined directory for presence of the new operation module.

18. An apparatus as recited in claim 15, wherein the detecting is achieved by the presence of data produced by a preregistering of the new operation module with the software.

19. An apparatus as recited in claim 15, wherein the detecting is achieved by manually calling the new operation module from within the software.

20. An apparatus as recited in claim 15, wherein the echocardiographic review station displays moving cardiac images stored in digital form.

21. An apparatus as recited in claim 15, wherein the new operation module comprises a module to execute along with software driving the echocardiographic review station, the module manipulating or performing calculations relating to digital images acquired by an ultrasound imaging device.

22. An apparatus as recited in claim 15, wherein the new operation module comprises a boundary detection operation which automatically detects a heart wall and other boundaries in an ultrasound image.

23. An apparatus as recited in claim 15, wherein the new operation module comprises an image analyzer which analyzes images produced by a color kinesis feature.

24. An apparatus as recited in claim 15, wherein the new operation module comprises a left ventricular volume calculation which analyzes a loop of images and calculates a volume of a left ventricle.

25. An apparatus as recited in claim 15, wherein the new operation module comprises a pisa calculation which calculates a surface area of a regurgitant jet.

26. An apparatus as recited in claim 15, wherein the new operation module comprises a speckle analysis which analyzes speckle in an image.

27. An apparatus as recited in claim 15, wherein the new operation module comprises a cardiac mass calculation which calculates a cardiac mass from an image.

28. An apparatus as recited in claim 15, wherein the new operation module comprises an acoustic densitometry calculation which calculates an acoustic densitometry of an image.

29. A computer readable storage medium storing a method for adding a new operation stored in a new operation module to software driving an echocardiographic review station, the method comprising:

detecting, by the echocardiographic review station, a presence of a new operation module not previously present in the software; and executing the new operation module from the software driving the echocardiographic review station.

30. A computer readable storage medium as recited in claim 29, wherein the executing occurs without reloading the software.

31. A computer readable storage medium as recited in claim 29, wherein the detecting checks a predetermined directory for presence of the new operation module.

32. A computer readable storage medium as recited in claim 29, wherein the detecting is achieved by the presence of data produced by a preregistering of the new operation module with the software.

33. A computer readable storage medium as recited in claim 29, wherein the detecting is achieved by manually calling the new operation module from within the software.

34. A computer readable storage medium as recited in claim 29, wherein the echocardiography viewing program displays moving cardiac images stored in digital form.

35. A computer readable storage as recited in claim 29, wherein the new operation module comprises a module to execute along with the software driving the echocardiographic review station, the module manipulating or performing calculations relating to digital images acquired by an ultrasound imaging device.

36. A computer readable storage medium as recited in claim 29, wherein the new operation module comprises a boundary detection operation which automatically detects a heart wall and other boundaries in an ultrasound image.

37. A computer readable storage medium as recited in claim 29, wherein the new operation module comprises an image analyzer which analyzes images produced by a color kinesis feature.

38. A computer readable storage medium as recited in claim 29, wherein the new operation module comprises a left ventricular volume calculation which analyzes a loop of images and calculates a volume of a left ventricle.

39. A computer readable storage medium as recited in claim 29, wherein the new operation module comprises a pisa calculation which calculates a surface area of a regurgitant jet.

40. A computer readable storage medium as recited in claim 29, wherein the new operation module comprises a speckle analysis which analyzes speckle in an image.

41. A computer readable storage medium as recited in claim 29, wherein the new operation module comprises a cardiac mass calculation which calculates a cardiac mass from an image.

42. A computer readable storage medium as recited in claim 29, wherein the new operation module comprises an acoustic densitometry calculation which calculates an acoustic densitometry of an image.

* * * * *